United States Patent
Kitschmann

Patent Number: 5,928,278
Date of Patent: Jul. 27, 1999

[54] DEFIBRILLATION ELECTRODE

[75] Inventor: Achim Kitschmann, Grenzach-Wyhlen, Germany

[73] Assignee: Sulzer Osypka GmbH, Grenzach-Wyhlen, Germany

[21] Appl. No.: 09/012,701

[22] Filed: Jan. 23, 1998

[30] Foreign Application Priority Data

Jan. 28, 1997 [EP] European Pat. Off. ............... 97810041

[51] Int. Cl.[6] ...................................................... A61N 1/05
[52] U.S. Cl. .......................................................... 607/129
[58] Field of Search .................................... 607/119, 129, 607/152; 600/374, 373

[56] References Cited

U.S. PATENT DOCUMENTS

| | | |
|---|---|---|
| 4,144,889 | 3/1979 | Tyers . |
| 5,350,419 | 9/1994 | Bendel et al. ............................ 607/119 |
| 5,411,527 | 5/1995 | Alt .......................................... 607/129 |

FOREIGN PATENT DOCUMENTS

| | | |
|---|---|---|
| 0 083 674 | 7/1983 | European Pat. Off. . |
| WO 92/07616 | 5/1992 | WIPO . |
| WO/95/19803 | 7/1995 | WIPO . |

*Primary Examiner*—Scott M. Getzow
*Attorney, Agent, or Firm*—Townsend and Townsend and Crew LLP

[57] ABSTRACT

The defibrillation electrode is intended for a temporary and epicardial use after heart operations. For the purpose of local stimulation of the surface of the heart the electrode comprises at its distal end a wire having a distal end which can be drawn out of an anchoring position. The stimulation wire or a plurality of stimulation wires is or are preformed in such a manner that it or they fractally covers or cover a global surface of influence largely uniformly and with relatively large radii of curvature. The surface of influence has a largely iso-diametral form.

13 Claims, 2 Drawing Sheets

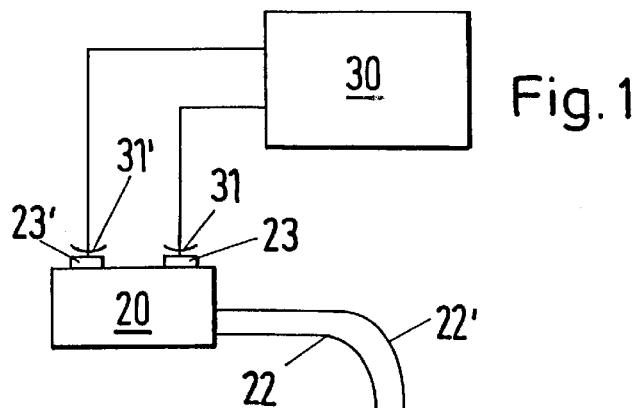
Fig. 1
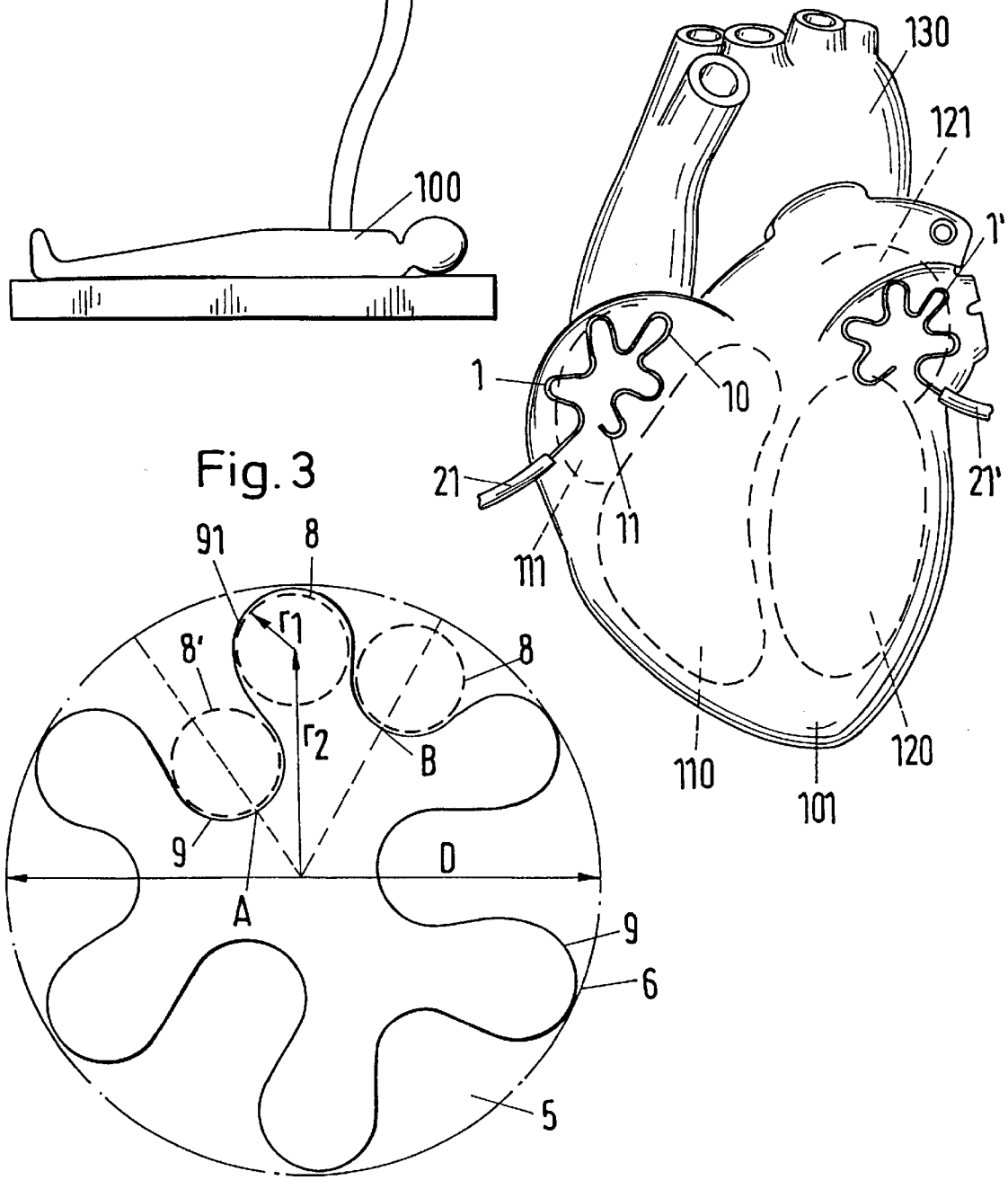
Fig. 2
Fig. 3

DEFIBRILLATION ELECTRODE

BACKGROUND OF THE INVENTION

1. Field of the Invention

The invention relates to a defibrillation electrode for use after heart operations for stimulation to the surface of the heart.

2. Description of the Prior Art

A system for the defibrillation of the heart is known from EP-A 0 636 385. This system is intended for a temporary use after heart operations. Two electrodes are implanted for a stimulation of the heart activity in the event that this is necessary due to a possible occurrence of auricular fluttering. Stimulation wires which are located at the distal ends of the electrodes are epicardially arranged over the auricles of the heart and anchored at the pericardium. In this arrangement, the wires each have distal ends which can be drawn out of anchoring positions. The temporary use of the defibrillation electrode is restricted to a few days after the operation; then a defibrillation is generally no longer necessary, so that the electrodes can be removed from the patient's body.

In the known system, the stimulation wire is a straight or gently curved piece of wire by means of which a strip of the surface of the auricle can be stimulated. A relatively large output of energy is necessary for the defibrillation. In order to avoid a damaging of the tissue which is in contact with the stimulation wire, the density of the output energy must not be too high.

SUMMARY OF THE INVENTION

The object of the invention is to provide measures with respect to the known defibrillation electrode as a result of which the density of the stimulation energy can be reduced. This object is satisfied by the electrode wherein the surface of influence is now no longer in the shape of a strip, but has a novel largely iso-diametral shape. The surface of influence is a unitary piece of surface which has approximately the same diameter D in all directions. It is fractally covered over by the preformed stimulation wire or by a plurality of preformed stimulation wires. The term "fractally covered" is understood to mean that only a part of the surface of influence is in direct contact with the wire and that the wire is spread out over the entire surface of influence.

The defibrillation electrode in accordance with the invention is intended for a temporary and epicardial use after heart operations. The electrode comprises at its distal end a wire which has a distal end which can be drawn out of an anchoring position for the purpose of local stimulation of the surface of the heart. The stimulation wire or wires is or are preformed in such a manner that it or they fractally covers or cover a global surface of influence largely uniformly and with relatively large radii of curvature. The surface of influence has a largely isodiametral form.

The local stimulation of the heart takes place at the contact surface of the wire. In contrast to this local stimulation, a global influence on the electrophysiological behavior of the auricle takes place at the surface of influence. This global surface of influence should be largely uniformly fractally covered; at the same time the wire or wires should have relatively large radii of curvature in order that the electrodes are easily removable from the patient's body.

The fractal covering by the stimulation wire or the stimulation wires means, in particular, the following: If only one stimulation wire is provided, then this should be formed in a meander shape, with the minimum radii of curvature of the wire advantageously not being substantially less than one tenth of D. If a plurality of stimulation wires is provided, these can be arranged in a bundle-like or fan-like manner. In this arrangement, at least individual ones of the stimulation wires can be not curved or only slightly curved; and/or at least individual wires can be corrugated.

In order that the auricle of the heart can be ideally stimulated, the surface of influence must be at least about 1000 mm$^2$ or—after conversion—have a diameter with a value D greater than 35 mm. In this arrangement, the wire surface for the local stimulation should be at least about 50 mm$^2$ in size. The output energy should—in relation to the surface of stimulation—have a density of at least about 0.1 J/mm$^2$ in order that a threshold is exceeded which triggers the defibrillation. The total length of the stimulation wire or of the stimulation wires is advantageously about 3 to 10 times greater than D. The diameter of the wire advantageously has a value in the range from 0.1 to 0.3 mm.

BRIEF DESCRIPTION OF THE DRAWINGS

FIG. 1 is a schematic illustration of a patient who is connected to an external defibrillator, FIG. 2 is a heart with stimulation wires arranged over the auricles, FIG. 3 is an auxiliary figure for the estimation of the geometrical relationships of a stimulation wire preformed in a meander shape.

DESCRIPTION OF THE PREFERRED EXEMPLARY EMBODIMENTS

Figure 4:
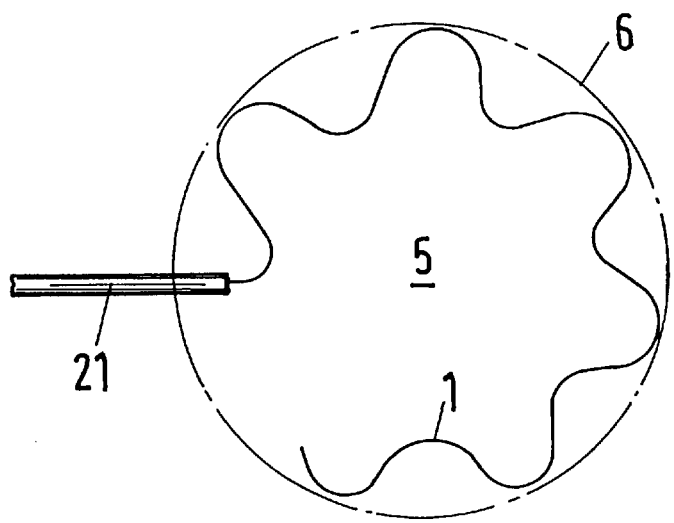
FIGS. 4–6 show examples for the execution of the stimulation wires.

FIG. 1 shows a patient 100 who is connected via two lines 22 and 22' and an intermediate device 20 to an external defibrillator 30. The defibrillator 30 is a conventional device by means of which a defibrillation can be performed by laying the surface electrodes 31 and 31' on the chest of the patient. The lines 22 and 22' produce the connection to two defibrillation electrodes 1 and 1' which are temporarily implanted in the heart 101 of the patient 100 (see FIG. 2) via the auricles 111 and 121. The intermediate device 20, namely a "limiter box", is constructed in such a manner that the stimulation energy can be limited to a maximum value of about 5 Joules. This maximum value is an amount of energy which is substantially smaller than the maximum amount of energy which could be produced by the defibrillator 30. The limiter box 20 has metallic contact surfaces 23 and 23' by means of which the surface electrodes 31 and 31' of the external defibrillator 30 can be brought into contact by laying them in place.

Instead of the named defibrillator 30, of course, a device constructed especially for implanted electrodes can also be provided in which no additional power limitation is required, so that the defibrillation electrodes can be connected directly to this device.

In the heart illustrated in FIG. 2, one recognizes the position of the heart chambers 110 and 120 in addition to those of the auricles 111 and 121. Various blood vessels are illustrated, with only the aorta 130 being provided with a reference numeral. In the defibrillation electrodes, the distal ends of the catheters 21, 21' can be seen in addition to the stimulation wires 1, 1'. These catheters 21, 21' connect the wires 1, 1' to the external, non-illustrated connection points at the proximal ends of the defibrillation electrodes; the lines 22, 22' can be connected to these connection points.

The wire 1 acts locally on the stimulation surface 10, which is given by the direct contact between the wire surface and the heart surface. In order to be able to secure the position of the wire, anchorings are to be provided. For this purpose the wire tip 11 can, for example, be pulled over a short length through the surface tissue of the epicardium. The wire 1 can, however, also be sutured in place. (cf. for this the named EP-A 0 636 385).

FIG. 3 shows a closed, symmetrical curve 9, which fractally covers over a circular area 5 (diameter D, periphery 6). The relationship which exists between the circumference U of the curve 9 and D can be simply determined for this curve 9: The curve 9 winds around twelve small circles 8 (radius $r_1$) arranged at the periphery 6 and six equally large circles 8' which are located in the middle region of the area 5. The partial segment 91 of the curve 9 between the points A and B is repeated 6 times. Each segment 91 is approximately ⅝ of the periphery of the small circle 8 in length. The diameter D has approximately 10 times the length of the radius $r_1$. Thus the result is: $U=1.5\pi D$. The circumference of the curve 9 is thus about 5 times greater than the diameter D.

The same relationships as for the curve 9 in FIG. 3 hold, with respect to the order of magnitude, for a stimulation wire 1 shaped in a meander-like manner. For electrodes with a plurality of stimulation wires the same relationship between the total wire length and the diameter of the surface of influence can also be provided. This relationship lies within the range between about 3 and 10. The minimum radius of curvature is governed by the condition that it should not be substantially less than the radius $r_1$ of the circles 8 ($\approx 0.1$ D).

Figure 5:
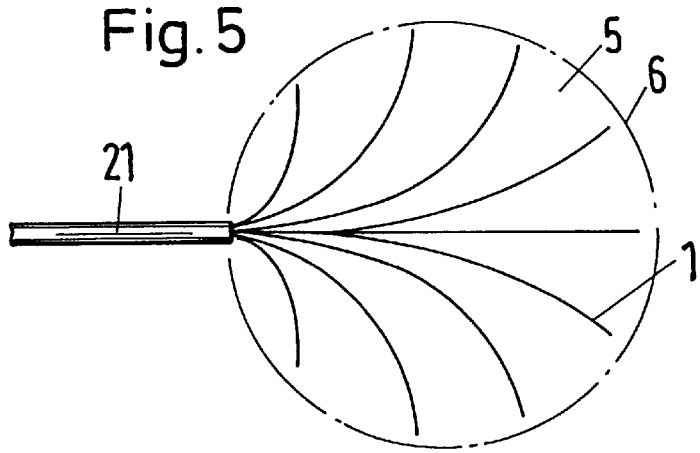
Figure 6:
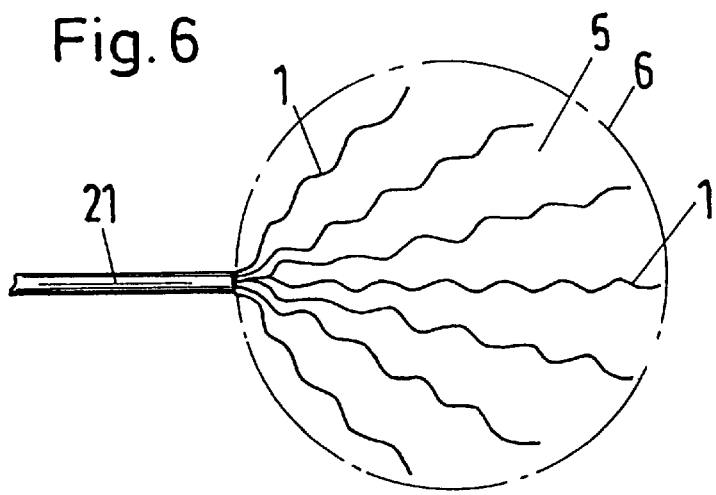

FIG. 4 shows an exemplary embodiment with a stimulation wire pre-shaped in a meander-like manner whose fractal covering of the surface of influence 5 is somewhat less uniform than in the curve 9 of FIG. 3. FIGS. 5 and 6 show electrodes with stimulation wires arranged in a brush-like or a fan-like manner, in one embodiment with wires which are not curved or are only slightly curved and in the other embodiment with corrugated wires.

Figure 7:
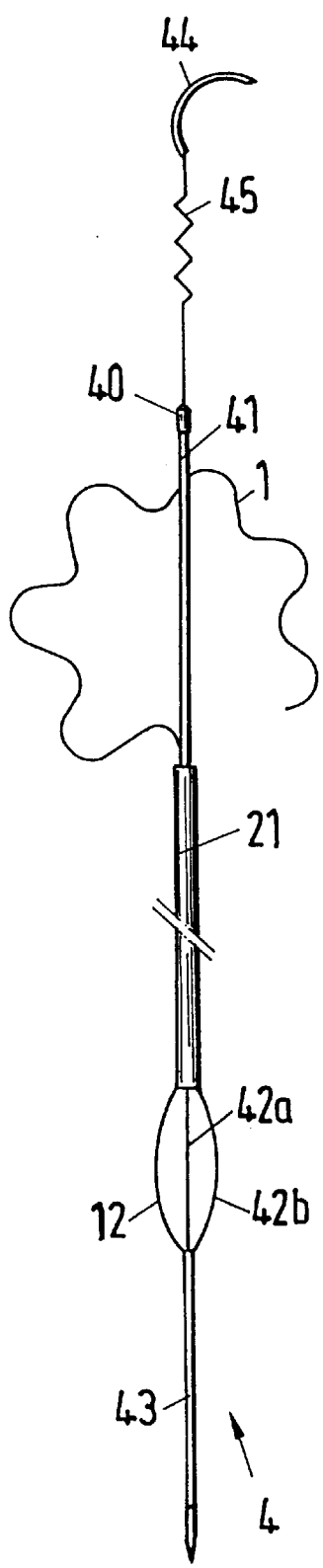
FIG. 7 is a combination of a heart wire with a defibrillation electrode.

The electrode 4 illustrated in FIG. 7 represents a heart wire which is combined with a defibrillation electrode (stimulation wire 1, catheter 21). The heart wire serves for the temporary monitoring and stimulation of the heart activity ("pacing") after a heart operation. It can be connected to an external heart pacemaker and/or to an ECG monitor).

The combination of a defibrillation electrode and a heart wire has, in addition to the stimulation wire or stimulation wires, electrode components for ECG measurements and for pacing. The heart wire comprises the following parts: a catheter 41 with electrical connections; two non-insulated wire lengths 42a and 42b which are provided as external connection points of the electrical connection; an electrode 40 in the form of a sleeve of platinum, by means of which an electrical contact to the heart muscle can be established; and a zig-zag-shaped plastic thread 45 by means of which the heart wire 4 can be anchored in the muscle. At the two ends of the heart wire 4 there are a chest needle 43 and a heart needle 44 respectively, which are surgical aids and which can each be clipped off after being put to use for its respective purpose. An external connection wire 12 of the stimulation wire 1 is connected to the HV-safe plug.

Corresponding means for anchoring can be provided at the defibrillation electrode, at the distal end or individual distal ends of the stimulation wire or wires, in a manner similar to the heart wire of the zig-zag-shaped plastic thread 45.

The line which connects the proximal end of the defibrillation electrode to the stimulation wire or the stimulation wires respectively must be a good electrical conductor. It advantageously has a core of silver and a jacket of stainless steel.

The combination of the defibrillation electrode and the heart wire is an advantageous embodiment of the invention. The subject of the invention is, however, also a defibrillation electrode without the additional components of a heart wire.

What is claimed is:

1. A defibrillation electrode for a temporary and epicardial use after heart operations comprising at its distal end, for the purpose of local stimulation of the surface of the heart:

at least one stimulation wire having a distal end that can be drawn out of an anchoring position;

wherein the at least one stimulation wire is preformed in such a manner that it fractally covers a global surface of influence largely uniformly and with relatively large radii of curvature;

wherein the surface of influence has a largely isodiametral form wherein the total length of the at least one stimulation wire is about 3 to 10 times greater than the average diameter D of the surface of influence; and wherein the diameter of the at least one wire has a value in the range from 0.1 to 0.3 mm.

2. A defibrillation electrode in accordance with claim 1 wherein the surface of influence is at least about 1000 $mm^2$ in size.

3. A defibrillation electrode in accordance with claim 1 wherein a wire surface for the local stimulation is at least about 50 $mm^2$ in size; and wherein a density of the output energy of at least about 0.1 $J/mm^2$ is provided, with this density being referred to the stimulation surface.

4. A defibrillation electrode in accordance with claim 1 wherein only one stimulation wire is provided, which is preformed in meander shape, with the minimum radii of curvature of the wire not being substantially less than one tenth of the average diameter D of the surface of influence.

5. A defibrillation electrode in accordance with claim 1 wherein a plurality of stimulation wires is provided which are arranged in a bundle-like or fan-like manner.

6. A defibrillation electrode in accordance with claim 5 wherein at least individual stimulation wires are substantially straight or at most only slightly curved.

7. A defibrillation electrode in accordance with claim 5 wherein at least individual stimulation wires each have an anchoring means at their ends.

8. A defibrillation electrode in accordance with claim 6 wherein at least individual ones of the stimulation wires are corrugated.

9. A defibrillation electrode in accordance with claim 1 wherein connection lines are arranged between a proximal end and the at least one stimulation wire and each have a core of silver and a jacket of stainless steel.

10. A defibrillation electrode in accordance with claim 1 wherein electrode parts for ECG measurements are provided in addition to the at least one stimulation wire.

11. A defibrillation electrode for a temporary and epicardial use after heart operations comprising at its distal end, for the purpose of local stimulation of the surface of the heart, one stimulation wire that is preformed in meander shape, with the minimum radii of curvature of the wire not being substantially less than one tenth of the average diameter D of the surface of influence.

12. An apparatus with two defibrillation electrodes, each defibrillation electrode comprising at its distal end, for the purpose of local stimulation to the surface of the heart:

at least one stimulation wire having a distal end that can be drawn out of an anchoring position;

wherein the at least one stimulation wire is preformed in such a manner that it fractally covers a global surface of influence largely uniformly and with relatively large radii of curvature;

wherein the surface of influence has a largely iso-diametral form wherein the total length of the at least one stimulation wire is about 3 to 10 times greater than the average diameter D of the surface of influence; and wherein the diameter of the at least one wire has a value in the range from 0.1 to 0.3 mm;

wherein the apparatus includes an energy source that is a conventional, extra-corporeally arranged defibrillator; and wherein the apparatus includes a device for the limitation of stimulation energy that is located between the defibrillator and the electrodes.

13. An apparatus in accordance with claim 12 wherein the device for the limitation of the stimulation energy limits the stimulation energy to a maximum value of approximately 5 Joules.

* * * * *